(12) United States Patent
Wang

(10) Patent No.: US 10,968,433 B2
(45) Date of Patent: Apr. 6, 2021

(54) METHOD FOR HARVESTING STEM AND PROGENITOR CELLS AND METHOD OF TREATMENT OF KIDNEY DISEASE AND NEUROLOGICAL DISEASE

(71) Applicant: Board of Supervisors of Louisiana State University and Agricultural and Mechanical College, Baton Rouge, LA (US)

(72) Inventor: Yuping Wang, Shreveport, LA (US)

(73) Assignee: BOARD OF SUPERVISORS OF LOUISIANA STATE UNIVERSITY, Baton Rouge, LA (US)

( * ) Notice: Subject to any disclaimer, the term of this patent is extended or adjusted under 35 U.S.C. 154(b) by 0 days.

(21) Appl. No.: 16/229,804

(22) Filed: Dec. 21, 2018

(65) Prior Publication Data

US 2019/0127706 A1 May 2, 2019

Related U.S. Application Data

(62) Division of application No. 15/178,746, filed on Jun. 10, 2016, now Pat. No. 10,160,955.

(60) Provisional application No. 62/186,463, filed on Jun. 30, 2015.

(51) Int. Cl.
| | | |
|---|---|---|
| *C12N 5/071* | (2010.01) | |
| *C12N 5/0797* | (2010.01) | |
| *A61K 35/22* | (2015.01) | |
| *A61K 35/30* | (2015.01) | |

(52) U.S. Cl.
CPC ......... *C12N 5/0687* (2013.01); *C12N 5/0623* (2013.01); *A61K 35/22* (2013.01); *A61K 35/30* (2013.01)

(58) Field of Classification Search
CPC .... C12N 5/0687; C12N 5/0623; A61K 35/30; A61K 35/22
See application file for complete search history.

(56) References Cited

U.S. PATENT DOCUMENTS 8,568,771 B2 * 10/2013 Cantaluppi ............... A61P 1/16
424/450

OTHER PUBLICATIONS

Lazzeri et al. Human Urine-Derived Renal Progenitors for Personalized Modeling of Genetic Kidney Disorders. J am Soc Nephrol (epub Jan. 2015), 26, 1961-1974 (Year: 2015).*

Lazzeri et al. J am Soc Nephrol (epub Jan. 2015), 26, 1961-1974—PubMed Abstract (Year: 2015).*
Ward et al. Adult human CD133/1+ kidney cells isolated from papilla integrate into developing kidney tubules. Biochimica et Biophysica Acta (2011), 1812, 1344-1357 (Year: 2011).*
Bussolati and Camussi. Therapeutic use of human renal progenitor cells for kidney regeneration. Nature Reviews Nephrology (epub. Aug. 2015), 35 page preprint. (Year: 2015).*
Zhao et al. Human Urine-Derived Renal Progenitors for Personalized Modeling of Genetic Kidney Disorders. Zhao et al. Reproductive Sciences (2011), 18(8), 772-780. (Year: 2011).*
Sigma Aldrich product A9909 (1999). (Year: 1999).*
Sun et al., "The Expression and Significance of Neuronal Iconic Proteins in Podocytes", PLOS One, Apr. 2014, v9(4), e93999.
Coskun et al., "CD133+ Neural Stem Cells in the Ependyma of Mammalian Postnatal Forebrain", PNAS, 2008, v105 (3), pp. 1026-1031.
Zhang et al., "Urine-Derived Stem Cells: A Novel and Versatile Progenitor Source for Cell-Based Therapy and Regenerative Medicine", Genes and Diseases, Jul. 2014, v1, pp. 8-17.
Hishikawa et al., "Adult Stem-Like Cells in Kidney", World Journal of Stem Cells, epub. Mar. 2015, v7(2), pp. 490-494.
Huang et al., "Caner Stem Cell-Like Characteristics of CD133+ Subpopulation in the J82 Human Bladder Cancer Cell Line", Molecular and Clinical Oncology, 2013, v1, pp. 180-184.
Kang et al., "Advanced Properties of Urine Derived Stem Cells Compared to Adipose Tissue Derived Stem Cells in Terms of Cell Proliferation, Immune Modulation and Multi Differentiation", Cell Therapy and Organ Transplantation, epub. Nov. 2015, v30, pp. 1764-1776.
Guan et al., "Biological Characteristics of Human-Urine-Derived stem Cells: Potential for Cell-Based Therapy in Neurology", Tissue Engineering Part A, Online Pub. May 15, 2014, v20(13-14), pp. 1794-1806.
D. Sulzer, "Multiple Hit Hypotheses for Dopamine Neuron Loss in Parkinson's Disease", Trends in Neurosciences, 2007, v30(5), pp. 244-250.
Vingerhoets et al., "Predictors of Cognitive Impairment in Advanced Parkinson's Disease", Journal Neurol Neurosurg Psychiatry, 2003, v74, pp. 793-796.
Wang et al., "Generation of Integration-Free Neural Progenitor Cells From Cells in Human Urine", Nature Methods, 2013, v10(1), pp. 84-89.

* cited by examiner

*Primary Examiner* — Sean C. Barron
(74) *Attorney, Agent, or Firm* — Davis & Bujold PLLC; Charles Holoubek; Michael J. Bujold

(57) ABSTRACT

A method of generating one of podocyte progenitor cells and neural stem/progenitor cells comprising the steps of collecting a urine specimen from a patient; centrifuging the urine specimen; and removing the one of podocyte progenitor cells and neural stem/progenitor cells.

17 Claims, 8 Drawing Sheets
(7 of 8 Drawing Sheet(s) Filed in Color)

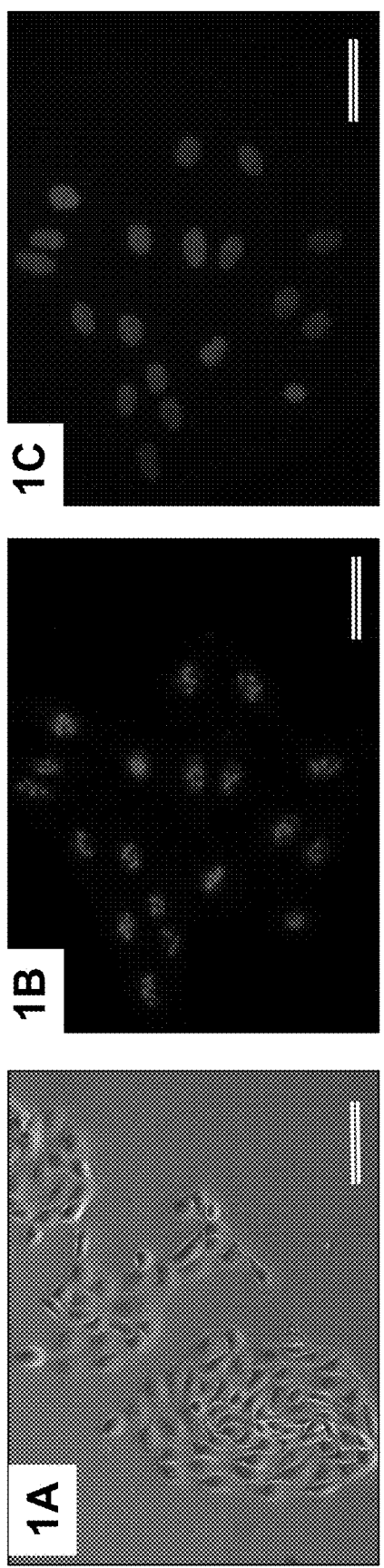
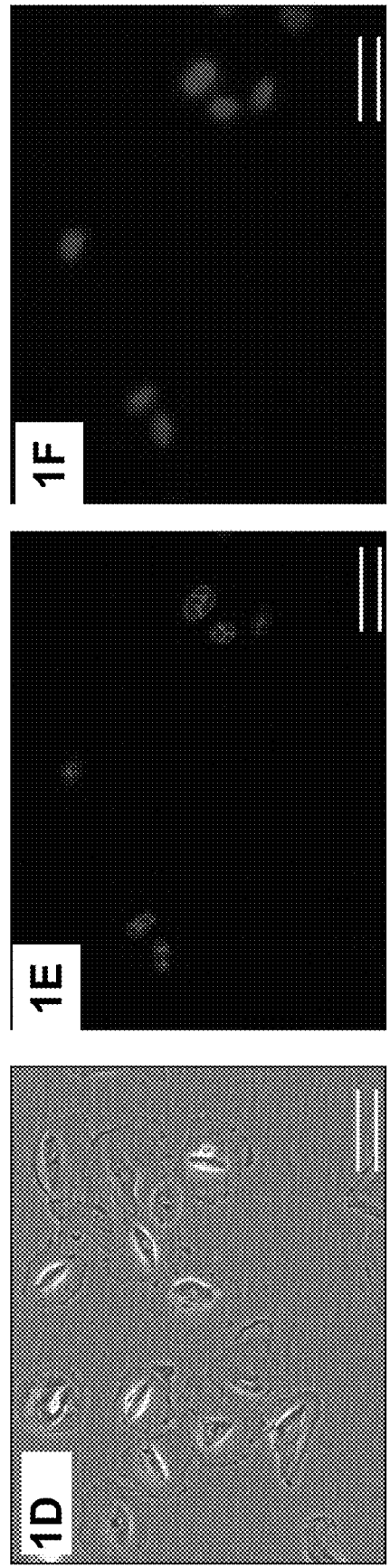
Figs. 1A - 1F

METHOD FOR HARVESTING STEM AND PROGENITOR CELLS AND METHOD OF TREATMENT OF KIDNEY DISEASE AND NEUROLOGICAL DISEASE

FIELD

The present process relates to collection and generation of podocyte progenitor cells and neuronal stem/progenitor cells from urine specimen and particularly the collection and generation of CD24+/CD133+/Oct-4+ podocyte progenitor cells and nestin+/SOX2+ neural stem/progenitor cells.

BACKGROUND

The kidney performs essential physiological roles ranging from metabolic waste excretion to homeostatic functions such as osmoregulation. Kidney diseases are currently a global public health problem, with an incidence that has reached epidemic proportions and continues to climb in the U.S. and worldwide. The increase in kidney diseases correlates with the rise in the aged population and the increasing prevalence of conditions that cause renal complications, such as cardiovascular disease, hypertension, and diabetes. Kidney diseases also result from congenital defects and from acquired conditions such as acute kidney injury (AKI) or chronic kidney disease (CKD). AKI involves a rapid loss of kidney function from sudden renal cell damage, which can be triggered by ischemia, toxins, or sepsis. CKD is typified by the progressive loss of kidney function over time due to fibrosis and the erosion of healthy tissue. Kidney disease leads to organ failure, known as end-stage renal disease (ESRD). Some current therapies for ESRD are renal replacement with dialysis or transplantation. These clinical managements for renal failure have a high mortality rate, necessitate intensive, long-term care, and place a considerable burden on patients and their families, and a tremendous socioeconomic strain on healthcare systems.

Glomerular diseases account for 90% of end stage renal disease at a cost of $20 billion per year in the U.S. According to the United States Renal Data System, there are approximately 26 million adults in the U.S. who have CKD, and there are 100,000 new patients who start on dialysis each year. $39 billion in direct U.S. costs each year are attributable to patients with end stage renal disease, which is associated with an approximate 20% mortality rate per year and an average life expectancy of a patient initiating dialysis of approximately four years.

Stem cell therapy, while offering exciting avenues for treatment of kidney disease, is problematic in the collection of stem cells. Bone marrow cells are a common source of stem cells, but accessing such cells is a very invasive procedure with significant risks.

SUMMARY

Wherefore, it is an object of the present invention to overcome the above mentioned shortcomings and drawbacks associated with the prior art.

Another object of the present invention is to provide a method of collecting, isolating, and culturing podocyte progenitor cells from urine.

A further object of the present invention is to provide a method of treating kidney disease, especially by collecting, isolating, and culturing podocyte progenitor cells from a patient's own urine and then implanting the podocyte progenitor cells into the kidney of the patient.

The present invention relates to devices and methods related to generating one of podocyte progenitor cells and neural stem/progenitor cells comprising the steps of collecting a urine specimen from a patient, centrifuging the urine specimen, and removing the one of podocyte progenitor cells and neural stem/progenitor cells.

The present invention also relates to devices and methods related to treating kidney disease in a patient comprising the steps of isolating podocyte progenitor cells from a urine specimen of the patient, growing the podocyte progenitor cells in vitro, and implanting the podocyte progenitor cells into a kidney of the patient. In additional embodiments of the present invention the kidney disease is a Glomerular disease. In additional embodiments of the present invention the kidney disease is related to podocyte loss.

The present invention also relates to devices and methods related to treating a central nervous system disease condition in a patient comprising the steps of isolating neural stem/progenitor cells from a urine specimen of the patient, growing the neural stem/progenitor cells in vitro, and implanting the neural stem/progenitor cells into the patient. In additional embodiments the central nervous system disease condition is one or more of Parkinson's disease, Huntington's disease, and multiple sclerosis. In additional embodiments of the present invention the neural stem/progenitor cells are implanted in the patient via intracerebral transplantation. In additional embodiments of the present invention the neural stem/progenitor cells are implanted in the patient via xenotransplantation. In additional embodiments the present invention further comprises the step of selecting cells that have positive expression for one of nestin and SOX2. In additional embodiments of the present invention the selected cells also have positive expression for podocin. In additional embodiments of the present invention the neural stem/progenitor cells are implanted into a central nervous system of the patient.

Various objects, features, aspects, and advantages of the present invention will become more apparent from the following detailed description of preferred embodiments of the invention, along with the accompanying drawings in which like numerals represent like components. The present invention may address one or more of the problems and deficiencies of the current technology discussed above. However, it is contemplated that the invention may prove useful in addressing other problems and deficiencies in a number of technical areas. Therefore the claimed invention should not necessarily be construed as limited to addressing any of the particular problems or deficiencies discussed herein.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The accompanying drawings, which are incorporated in and constitute a part of the specification, illustrate various embodiments of the invention and together with the general description of the invention given above and the detailed description of the drawings given below, serve to explain the principles of the invention. It is to be appreciated that the accompanying drawings are not necessarily to scale since the emphasis is instead placed on illustrating the principles of the invention. The invention will now be described, by way of example, with reference to the accompanying drawings in which:

FIGS. 1A-1F are six photographs of cells collected from urine showing proliferation potential, Urine cells in culture and stained with Ki67, Ki67 is a cell proliferation marker, DAPI stains nuclear, where FIGS. 1A-1C are primary cultured cell, FIG. 1A shows clone formation within one week after seeding, bar=200 µm; FIG. 1B shows Ki67 staining and FIG. 1C shows DAPI staining, bar=100 µm in FIGS. 1B and 1C; FIGS. 1D-1F are after first passage, FIG. 1D shows cells under phase contrast, bar=100 µm; FIG. 1E shows Ki67 staining and FIG. 1F shows DAPI staining, bar=50 µm in FIGS. 1E and 1F; positive staining of Ki67 indicates urine cells are proliferative;

FIGS. 5C and 5D showing podoplanin; and FIGS. 5E and 5F showing partitioning defective 3 homolog (PARD3); nephrin is a foot process slit adhesion protein expressed in podocytes; podoplanin is a podocyte protein; PARD3 is a polarity protein; expression of nephrin, podoplanin, and PARD3 in urine cells after prolonged culture indicates that urine cells could differentiate into mature podocytes;

FIG. 6B shows a 7,000 magnification of cells where enriched foot processes can be seen after prolonged/long term culture, and FIG. 6C shows a 30,000 magnification of foot processes of FIG. 6B

DETAILED DESCRIPTION OF THE INVENTION

Figure 2A:
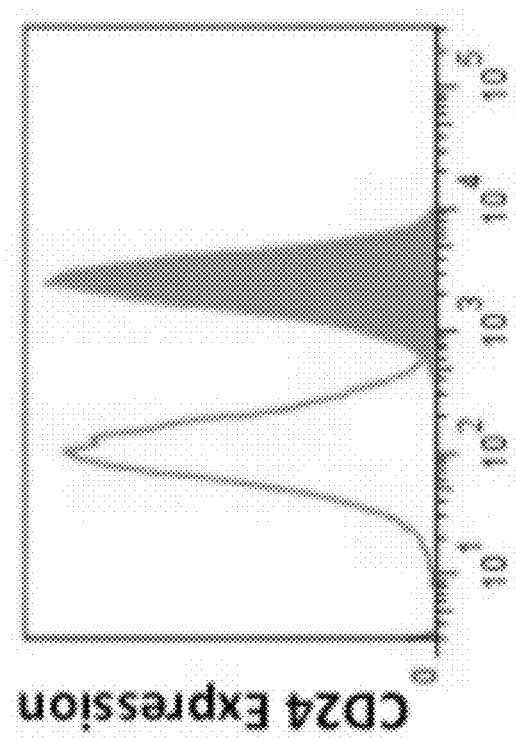
FIGS. 2A and 2B are three photographs and a graph showing cells collected from urine express podocyte progenitor cell marker CD24, FIG. 2A showing CD24 expression by immunofluorescent staining and FIG. 2B showing CD24 expression by flow-cytometry with the lined/hollow curve to the left showing unstained and the filed curve to the right showing CD24 stained.

The present invention will be understood by reference to the following detailed description, which should be read in conjunction with the appended drawings. It is to be appreciated that the following detailed description of various embodiments is by way of example only and is not meant to limit, in any way, the scope of the present invention. In the summary above, in the following detailed description, in the claims below, and in the accompanying drawings, reference is made to particular features (including method steps) of the present invention. It is to be understood that the disclosure of the invention in this specification includes all possible combinations of such particular features, not just those explicitly described. For example, where a particular feature is disclosed in the context of a particular aspect or embodiment of the invention or a particular claim, that feature can also be used, to the extent possible, in combination with and/or in the context of other particular aspects and embodiments of the invention, and in the invention generally. The term "comprises" and grammatical equivalents thereof are used herein to mean that other components, ingredients, steps, etc. are optionally present. For example, an article "comprising" (or "which comprises") components A, B, and C can consist of (i.e., contain only) components A, B, and C, or can contain not only components A, B, and C but also one or more other components. Where reference is made herein to a method comprising two or more defined steps, the defined steps can be carried out in any order or simultaneously (except where the context excludes that possibility), and the method can include one or more other steps which are carried out before any of the defined steps, between two of the defined steps, or after all the defined steps (except where the context excludes that possibility).

The term "at least" followed by a number is used herein to denote the start of a range beginning with that number (which may be a range having an upper limit or no upper limit, depending on the variable being defined). For example "at least 1" means 1 or more than 1. The term "at most" followed by a number is used herein to denote the end of a range ending with that number (which may be a range having 1 or 0 as its lower limit, or a range having no lower limit, depending upon the variable being defined). For example, "at most 4" means 4 or less than 4, and "at most 40% means 40% or less than 40%. When, in this specification, a range is given as "(a first number) to (a second number)" or "(a first number)-(a second number)," this means a range whose lower limit is the first number and whose upper limit is the second number. For example, 25 to 100 mm means a range whose lower limit is 25 mm, and whose upper limit is 100 mm. The embodiments set forth the below represent the necessary information to enable those skilled in the art to practice the invention and illustrate the best mode of practicing the invention. In addition, the invention does not require that all the advantageous features and all the advantages need to be incorporated into every embodiment of the invention.

Turning now to FIGS. 1-6, a brief description concerning the various components of the present invention will now be briefly discussed. The inventors were able to culture/generate podocyte stem/progenitor cells in vitro from urine specimen. Urine could be used as a rich source of podocyte progenitor cells. This method of obtaining progenitor cells is much more patient friendly and carries much fewer dangers and complications as, for example, collecting cells from the patient's bone marrow. Urine is a bodily waste and easy to collect, and thus this method of harvesting progenitor cells is significantly less invasive for the patient than many other methods currently used. Additionally, by isolating and culturing podocyte progenitor cells directly, this allows for a more direct application of cells to the patient's kidney, rather than stem cells that must be differentiated first. These cells are pertinent for renewal, restoration, and regeneration of kidney cell function and for the regeneration medicine, by, for example, restoring lost glomerular podocytes in vivo by treating a damaged podocyte population with the a cell population containing podocyte progenitor cells derived from the patient's own urine.

Podocyte progenitor cells were extracted from a urine specimen, and podocyte progenitor cells were then characterized. A freshly obtained urine specimen was centrifuged at 1,500 rpm at 4° C. for 5 minutes. Cell pellets were suspended and washed twice with medium RPMI media1640 (GIBCO) containing 1% antibiotic-antimycotic solution. Cell pellets were obtained again by centrifugation and then resuspended in RPMI media 1640 containing fetal bovine serum, ITS solution (insulin, transferrin, and selenium), and antibiotic-antimycotic solution. Cell suspension was seeded in cell culture plate or flask and incubated in a 37° C. cell culture incubator with 5% $CO_2$ and air. After overnight incubation, the plate was washed twice with phosphate buffered saline (PBS) and fresh RPMI media 1640 with supplements was replaced. The medium was changed every other day. Turning to FIGS. 1A-1F, a cell clone was defined as a cell aggregate containing at least five cells per clone, as shown in FIGS. 1A and 1D. Proliferation potential of urine cells was confirmed by Ki67 staining, as shown in FIGS. 1B and 1E. Ki67 is a cell proliferation marker. Stem cell/podocyte progenitor cell was characterized by positive expression of CD24, CD133, Oct-4, and podocin by immune-fluorescent staining or by flow cytometry. CD24, CD133, and Oct-4 are stem cell/progenitor cell markers. Podocin is a podocyte marker. The results are shown in FIGS. 1A to 6C.

Figure 2B:
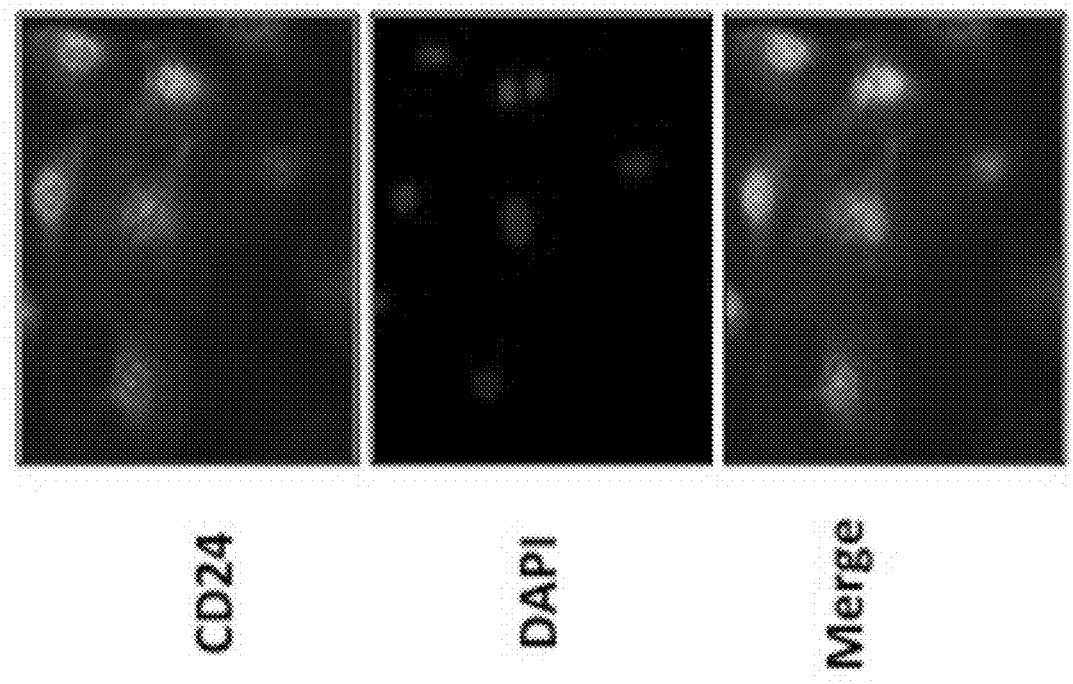

FIG. 2 shows expression of CD24 in cells from the urine specimen. FIG. 2A shows CD24 expression by fluorescent staining. FIG. 2B shows CD24 expression by flow cytometry. CD24 is a podocyte progenitor cell marker.

Figure 3:
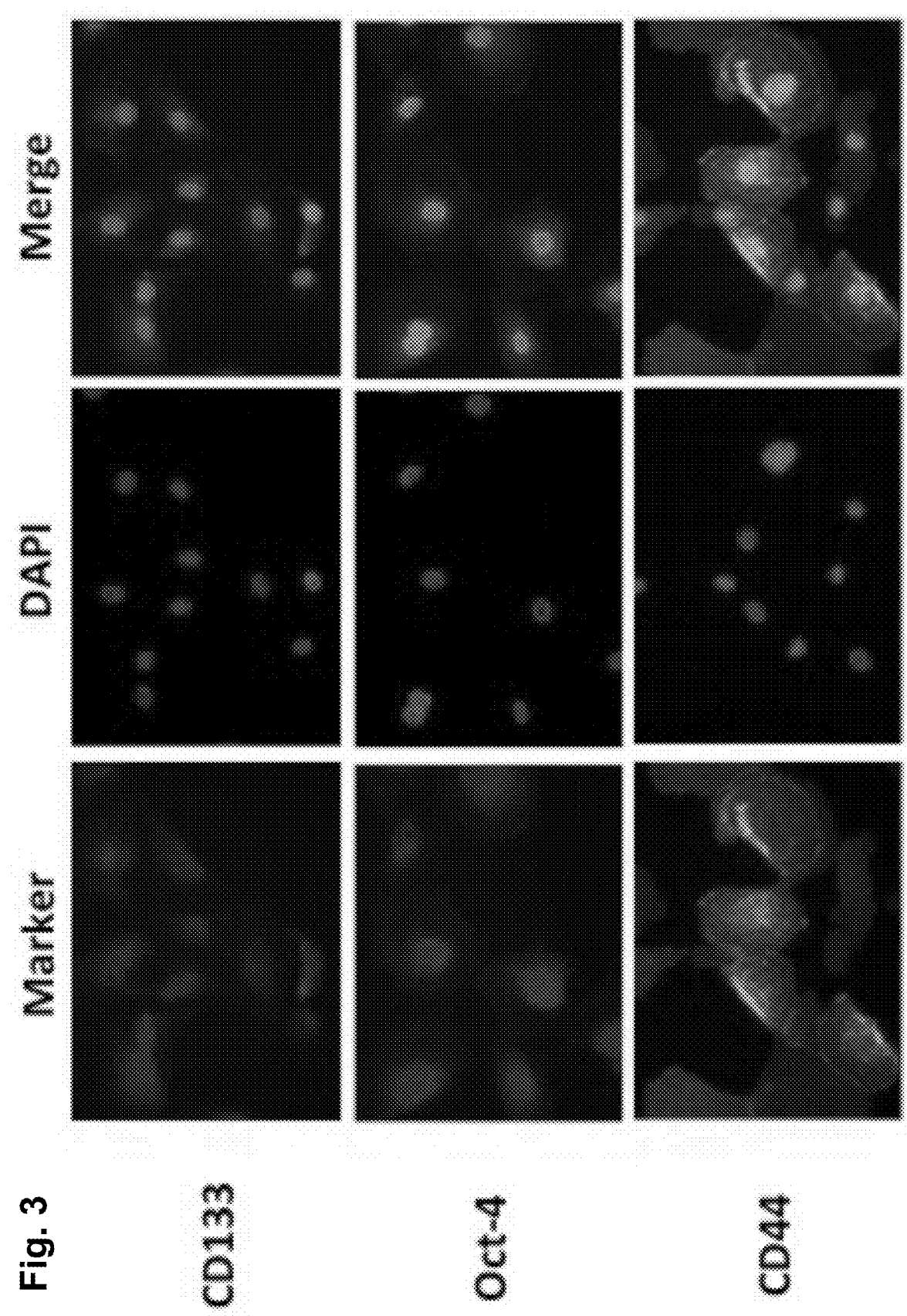
FIG. 3 is nine photographs showing cells collected from urine express podocyte stem cell/progenitor cell markers CD133, Oct-4, and CD44; CD133 and Oct-4 are stem cell/progenitor cell markers and CD44 is a parietal epithelial cell marker.

FIG. 3 shows expression of each of CD133, Oct-4, and CD44 in cells from the urine specimen. CD133 and Oct-4 are stem cell/progenitor cell markers. CD44 is a parietal epithelial cell activation marker.

Figures 4A, 4B, 4C:
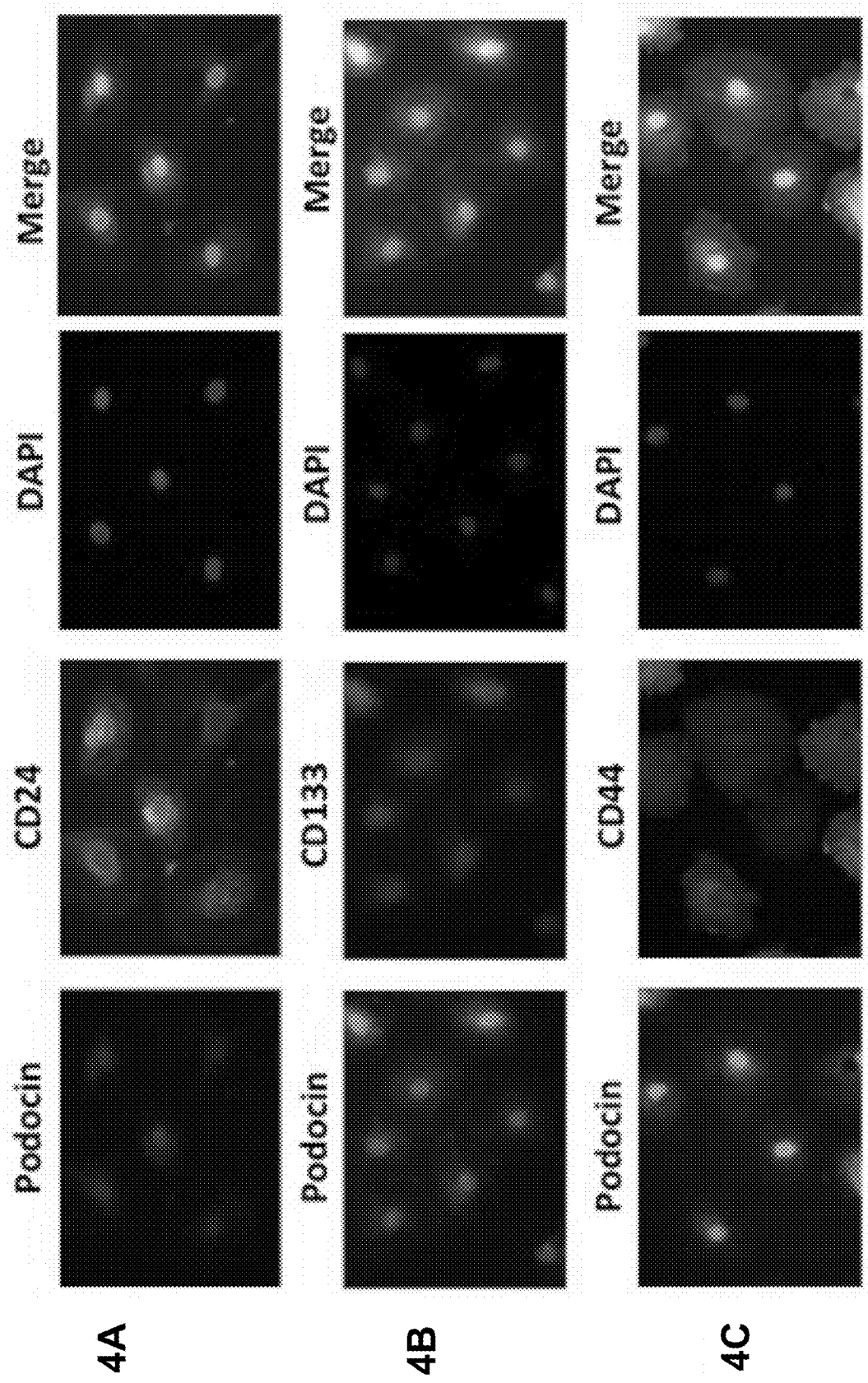
FIGS. 4A-4C are twelve photographs showing cells collected from urine co-express podocyte and stem cell/progenitor cell markers CD24, CD133, and CD44 respectively; podocin is a podocyte marker.
Figure 5A:
FIGS. 5A-5F are six photographs sowing differentiation potential of urine cells into podocytes after prolonged culture, with FIGS. 5A and 5B showing nephrin.
Figure 5B:
Figure 5C:
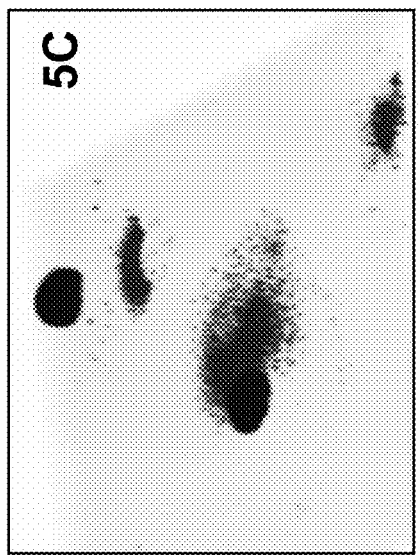
Figure 5D:
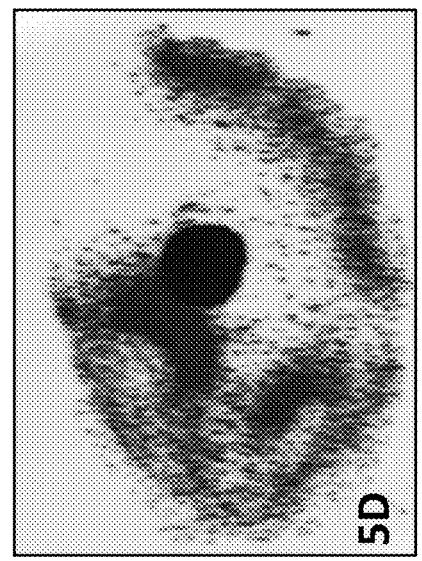
Figure 5E:
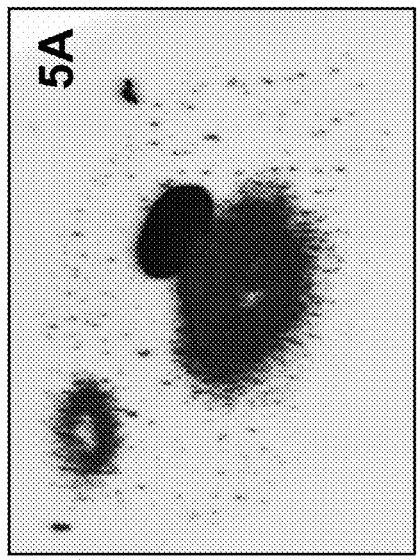
Figure 5F:
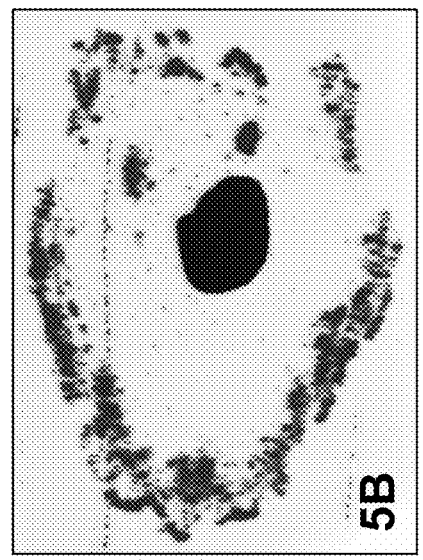

FIG. 4 shows co-expression of podocyte and stem cell/progenitor cell markers in cells from the urine specimen. Podocin is a podocyte marker. FIG. 4A shows co-expression of podocin and CD24. FIG. 4B shows co-expression of podocin and CD133. FIG. 4C shows co-expression of podocin and CD44. This data shows that these cells are podocyte progenitor cells.

FIG. 5 shows the differentiation of urine cells into podocytes after prolonged culture. FIGS. 5A and 5B show expression of nephrin over time, a transmembrane protein that is a structural component of the slit diaphragm and expressed in podocytes. FIGS. 5C and 5D show expression of podoplanin over time, a type-I, integral membrane, heavily O-glycosylated glycoprotein expressed in podocytes. FIGS. 5E and 5F show expression of PARD3 over time, an adapter protein involved in asymmetrical cell division and cell polarization processes. The presence of all of these proteins indicates that the collected podocyte progenitor urine cells had differentiated in mature podocytes.

Figures 6A, 6B, 6C:
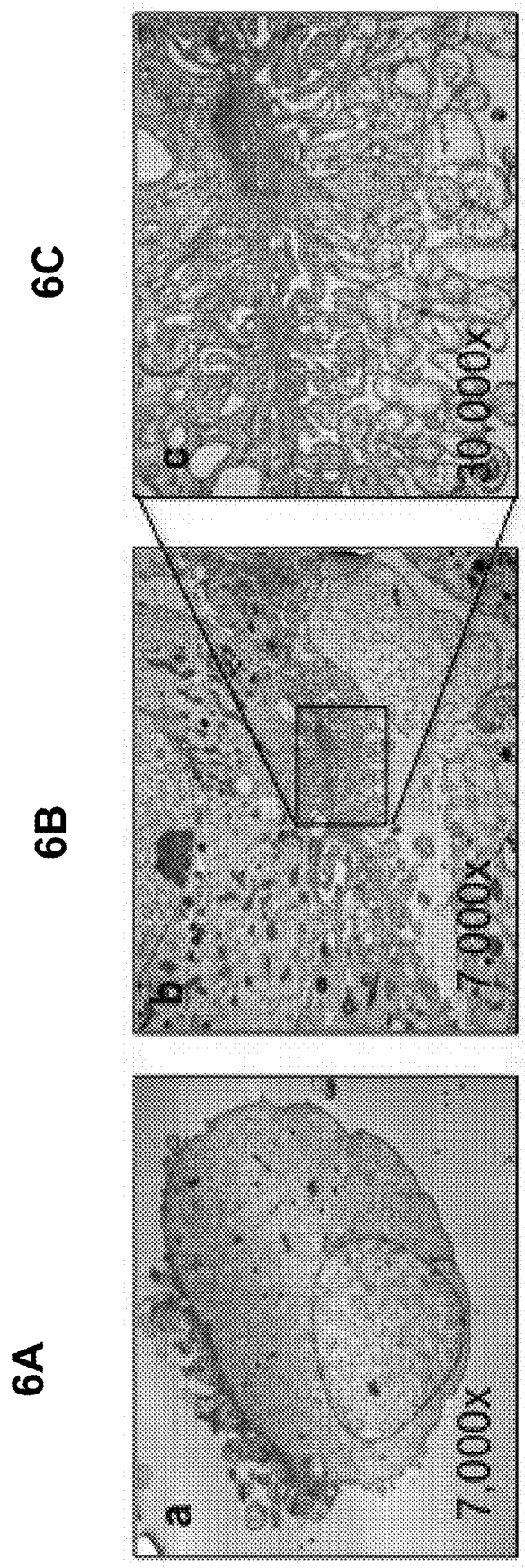
FIG. 6A-6C are three photographs of electron microscopy showing differentiation potential of urine cells, with FIG. 6A showing a 7,000 magnification of cells at proliferative stage (short term culture) that lacks a foot process.

Turning to FIG. 6, this Figure shows the differentiation of the collected podocyte progenitor urine cells. As shown in FIG. 6A, an electron micrograph photo of a short term culture, little podocyte foot processes have formed. However, as shown in FIGS. 6B and 6C, electron micrograph photos of a long term culture, are clear indication that podocyte foot processes have formed, and that the cells have, in fact, differentiated into podocyte cells.

Podocytes are critical components of the kidney glomerular barrier. Typically, loss of podocytes in a patient leads to massive proteinuria and glomerular barrier dysfunction. By collecting podocytes progenitor cells from urine, a relatively non-invasive avenue is opened to treat kidney disease related to podocyte loss.

Neuronal Stem/Progenitor Cell

In continuing experiments, additional urine cells were collected by the process above and were screened for the presence of neural stem/progenitor cells (NSPCs). Much to the surprise of the inventor, NSPCs were found to be present. The urine cells expressed NSPC marker nestin and SOX2. Nestin is a neuroectodermal stem cell marker. Nestin expression has been extensively used as a marker for central nervous system (CNS) progenitor cells in different contexts. Nestin is best known as the neuronal precursor cells of the subgranular zone.

SOX2 is a transcription factor and plays a critical role in maintenance of embryonic and neutral stem cells. Cells expressing SOX2 are capable of both producing cells identical to themselves and differentiated into neural cell types and both are hallmarks of stem cells. Emerging evidence also shows that SOX2 expressing cells hold great promise in the field of neuron regenerative medicine.

Cell death is a characteristic of acute CNS disorders as well as neurodegenerative disease. The loss of cells is amplified by the lack of regenerative abilities for cell replacement and repair in the CNS. One way to circumvent this is to use cell replacement therapy via regenerative neural stem cells (NSCs). NSCs can be cultured in vitro as neurospheres in a manner known in the art. These neurospheres are composed of NSPCs with growth factors such as EGF and FGF. The withdrawal of these growth factors activate differentiation into neurons, astrocytes, or oligodendrocytes which can be transplanted within the brain at the site of injury. The benefits of this therapeutic approach have been examined in Parkinson's disease, Huntington's disease, and multiple sclerosis. NSPCs induce neural repair via intrinsic properties of neuroprotection and immunomodulation. Some possible routes of transplantation include intracerebral transplantation and xenotransplantation. Other methods of cultivation of and treatment with neural stem cells are known in the art, including in U.S. Pat. No. 7,635,467, the disclosure of which is incorporated herein.

Figure 7:
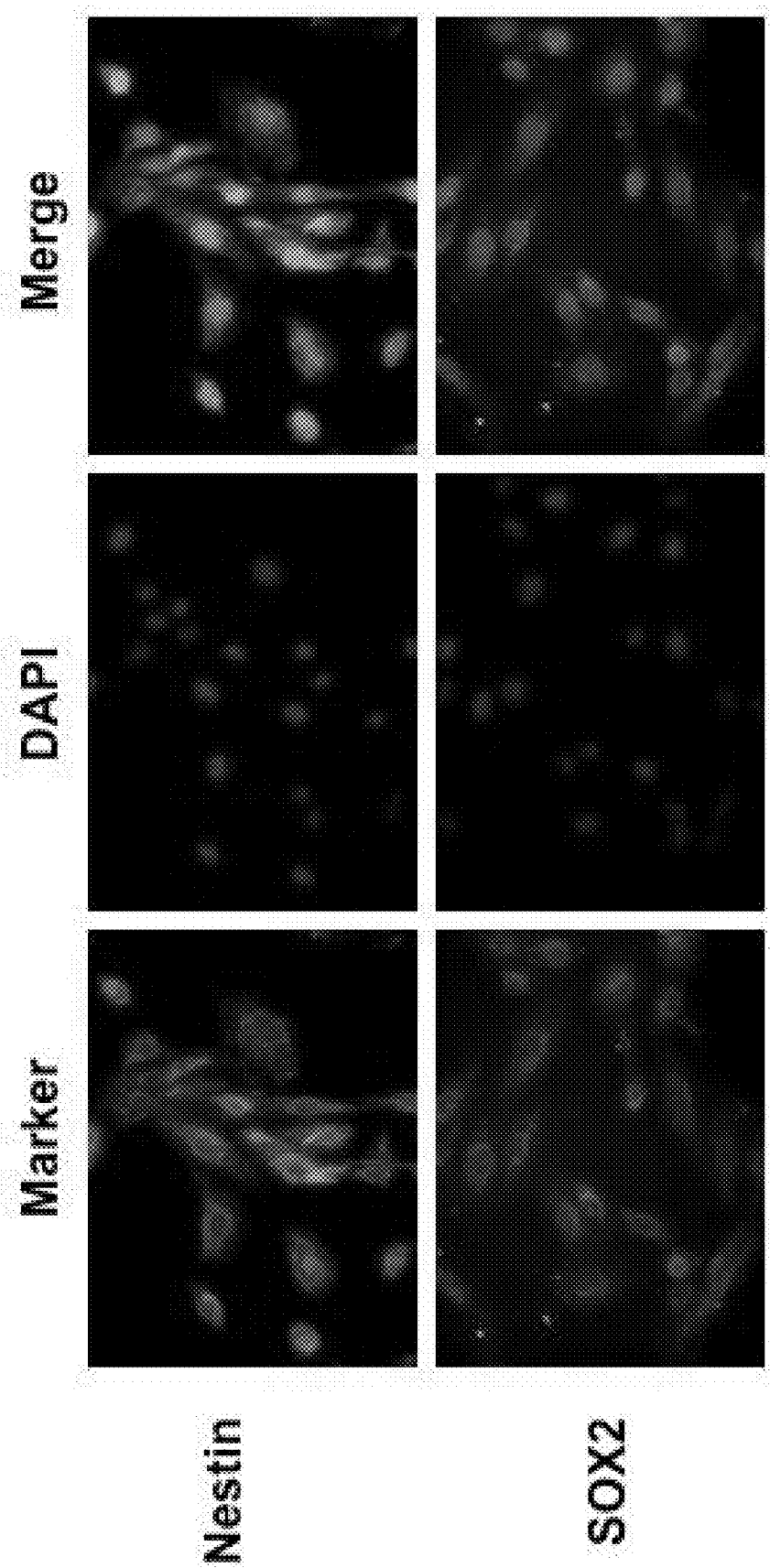
FIG. 7 is six photographs showing urine cells expressing neural stem/progenitor cell markers nestin and SOX2; nestin is a neuroectodermal stem cell marker; SOX2 is a transcription factor that is essential for maintaining self-renewal and plays a critical role in maintenance of embryonic and neutral stem cells.
Figure 8:
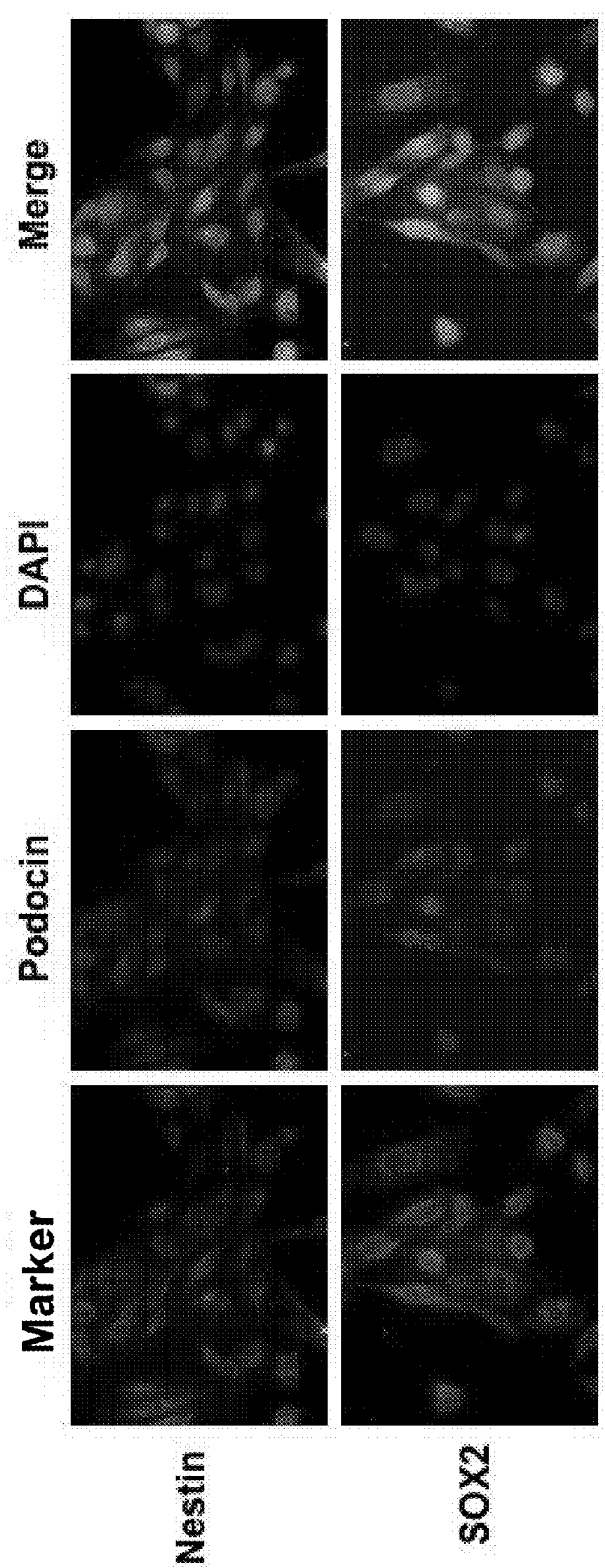
FIG. 8 is eight photographs showing co-expression of nestin and SOX2 with podocin in urine cells; podocin is a podocyte marker; co-expression of nestin/podocin and SOX2/podocin indicates that nestin and SOX2 expressing urine cells have a great potential to differentiate neuronal linage cells.

As shown in FIG. 7, urine cells express neuronal stem/progenitor cell markers nestin and SOX2. Nestin is a neuroectodermal stem cell marker. SOX2 is a transcription factor that maintains self-renewal and plays a critical role in maintenance of embryonic and neutral stem cells. FIG. 8 shows co-expression of nestin and SOX2 with podocin in urine cells. Podocin is a podocyte marker. Co-expression of nestin/podocin and SOX2/podocin indicate that nestin and SOX2 expressing urine cells have a great potential to differentiate neuronal linage cells. The ability to harvest NSPCs from urine offers an unexpected leap forward in the ability to treat CNS conditions. Urine cell expression of neuronal stem/progenitor cell marker nestin and SOX2 indicate that these nestin and SOX2 expressing urine cells hold a great promise in the field of neuron regenerative medicine.

The invention illustratively disclosed herein suitably may explicitly be practiced in the absence of any element which is not specifically disclosed herein. While various embodiments of the present invention have been described in detail, it is apparent that various modifications and alterations of those embodiments will occur to and be readily apparent those skilled in the art. However, it is to be expressly understood that such modifications and alterations are within the scope and spirit of the present invention, as set forth in the appended claims. Further, the invention(s) described herein is capable of other embodiments and of being practiced or of being carried out in various other related ways. In addition, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items while only the terms "consisting of" and "consisting only of" are to be construed in the limitative sense.

I claim:

1. A method of treating kidney disease in a patient comprising the steps of:
   isolating podocyte progenitor cells from a urine specimen of the patient;
   growing the podocyte progenitor cells in vitro; and
   selecting the podocyte progenitor cells that have positive expression for CD133; and
   implanting the podocyte progenitor cells into a kidney of the patient.

2. The method of claim 1 wherein the kidney disease is a Glomerular disease.

3. The method of claim 1 wherein the kidney disease is related to podocyte loss.

4. The method of claim 1, further comprising
   centrifuging the urine specimen at 1,500 rpm at 4° C. for 5 minutes;
   washing suspended cell pellets twice with medium RPMI media1640 containing 1% antibiotic-antimycotic solution;
   centrifuging again to obtain cell pellets again;
   resuspend cell pellets in RPMI media 1640 containing fetal bovine serum, ITS solution containing insulin, transferrin, and selenium, and antibiotic-antimycotic solution;
   seeding cell suspension in a cell culture plate or flask and incubate in a 37° C. cell culture incubator with 5% CO2 and air overnight;
   washing the plate or flask twice with phosphate buffered saline (PBS) after overnight incubation; and
   replacing fresh RPMI media 1640 with supplements.

5. The method of claim 1 further comprising the steps of:
   collecting a urine specimen from a patient;
   centrifuging the urine specimen; and
   removing the podocyte progenitor cells.

6. The method of claim 5 further comprising the step of screening for the podocyte progenitor cells.

7. The method of claim 5 further comprising the step of culturing the podocyte progenitor cells until the podocyte progenitor cells express partitioning defective 3 homolog (PARD3), nephrin, and podoplanin.

8. The method of claim 5 further comprising the step of selecting cells that have positive expression for one of nestin and SOX2.

9. The method of claim 8 wherein the selected cells also have positive expression for podocin.

10. The method of claim 5 further comprising the step of selecting the podocyte progenitor cells that have positive expression for Oct-4.

11. The method of claim 5 wherein the podocyte progenitor cells are grown in vitro in a medium including insulin, transferrin, and selenium.

12. The method of claim 11 wherein the medium further includes RPMI medium 1640 and the selected cells also have positive expression for, Oct-4, nestin, and SOX2.

13. The method of claim 5 wherein the podocyte progenitor cells are grown in vitro in a medium including RPMI medium 1640.

14. The method of claim 5 wherein the podocyte progenitor cells are grown in vitro in a medium in the absence of any growth factors.

15. The method of claim 5 wherein the podocyte progenitor cells are grown in vitro in a medium in the absence of any one or more of the following four growth factors: human epidermal growth factor (hEGF), platelet-derived growth factor (PDGF), transforming growth factor- (TGF-), or basic fibroblast growth factor (bFGF).

16. The method of claim 5 wherein the podocyte progenitor cells are grown in vitro in a medium in the absence of all four of the following growth factors: human epidermal growth factor (hEGF), platelet-derived growth factor (PDGF), transforming growth factor- (TGF-), and basic fibroblast growth factor (bFGF).

17. The method of claim 5 further comprising restoring lost glomerular podocytes in vivo by treating a damaged podocyte population of the patient with the a cell population containing the podocyte progenitor cells that have positive expression for CD133.

* * * * *